United States Patent [19]
Rohde, Jr. et al.

[11] Patent Number: 6,099,844
[45] Date of Patent: Aug. 8, 2000

[54] INCREASING YIELD OF EXTRACTABLE SUBSTANCES FROM BOTANICALS WITH AN ENZYME COMPOSITION

[75] Inventors: Rodger R. Rohde, Jr., Wayne; Chris Rohde, Ringwood, both of N.J.; Edward F. Schuler, Keswick, Va.; Richard A. Handel, Ridgewood, N.J.

[73] Assignee: TRIARCO Industries, Inc., Wayne, N.J.

[21] Appl. No.: 08/928,656

[22] Filed: Sep. 12, 1997

(Under 37 CFR 1.47)

Related U.S. Application Data

[63] Continuation of application No. 08/294,115, Aug. 22, 1994, abandoned.

[51] Int. Cl.[7] ............................. A01N 65/00; A23B 7/10; A61K 38/54; A61K 38/43
[52] U.S. Cl. .................. 424/195.1; 424/94.1; 424/94.2; 426/49; 426/51; 426/52; 435/99; 435/200; 435/209
[58] Field of Search ................................. 424/94.2, 94.1, 424/195.1; 426/49, 51, 52; 435/99, 200, 209

[56] References Cited

U.S. PATENT DOCUMENTS

| 5,057,321 | 10/1991 | Edgren et al. | 424/439 |
|---|---|---|---|
| 5,424,299 | 6/1995 | Monte | 514/54 |
| 5,723,328 | 3/1998 | Dallboege et al. | 435/209 |

FOREIGN PATENT DOCUMENTS

| 1107824 | 3/1968 | United Kingdom . |
|---|---|---|

OTHER PUBLICATIONS

Foods Chemical Codex, National Academy Press, 3rd Ed., 1981, pp. 479–484, 490–491.

*Primary Examiner*—David M. Naff
*Assistant Examiner*—Deborah K. Ware
*Attorney, Agent, or Firm*—Fitzpatrick, Cella, Harper & Scinto

[57] ABSTRACT

This invention relates to a method of increasing the yield of extractable substance from a botanical in the gastrointestinal system of a human being comprising the step of ingesting an enzyme composition comprising a cellulase enzyme and a pectinase enzyme at approximately the same time as a botanical is ingested so that the cellulase and pectinase enzymes degrade the cellulosic and pectin constituents, respectively, contained in the ingested botanical, to obtain an enhanced quantity of extractable substance from the botanical. Another method of use embodiment of this invention comprises the step of ingesting an enzyme composition comprising a cellulase enzyme, a pectinase enzyme, a hemicellulase enzyme and a xylanase enzyme at approximately the same time as a botanical is ingested, to obtain an enhanced quantity of extractable substance from the botanical. The corresponding botanical food composition method of use embodiment of this invention comprises the step of ingesting a botanical food composition comprising a botanical, a cellulase enzyme, a pectinase enzyme, a hemicellulase enzyme and a xylanase enzyme, wherein the cellulase, pectinase, hemicellulase and xylanase enzymes degrade the cellulosic, pectin, hemicellulosic and xylan constituents, respectively, contained in the ingested botanical, to obtain an enhanced quantity of extractable substance from the botanical.

20 Claims, No Drawings

INCREASING YIELD OF EXTRACTABLE SUBSTANCES FROM BOTANICALS WITH AN ENZYME COMPOSITION

This application is a continuation of application Ser. No. 08/294,115 filed Aug. 22, 1994, now abandoned.

FIELD OF THE INVENTION

This invention relates to a method of increasing the yield of an extractable substance from a botanical in the gastrointestinal system of a human being comprising the step of ingesting an enzyme composition comprising a cellulase enzyme and a pectinase enzyme at approximately the same time as a botanical is ingested so that the cellulase and pectinase enzymes degrade the cellulosic and pectin constituents, respectively, contained in the ingested botanical, to obtain an enhanced quantity of extractable substance from the botanical. In another method of use embodiment, this invention comprises the step of ingesting the above-mentioned enzyme composition further comprising a hemicellulase enzyme which degrades the hemicellulosic constituents contained in the ingested botanical, to obtain an enhanced quantity of extractable substance from the botanical. In yet another method of use embodiment, this invention comprises the step of ingesting the above-mentioned enzyme composition further comprising a xylanase enzyme which degrades the xylan constituents contained in the ingested botanical, to obtain an enhanced quantity of extractable substance from the botanical.

This invention also relates to a method of increasing the yield of an extractable substance from a botanical in the gastrointestinal system of a human being comprising the step of ingesting a botanical food composition comprising a botanical, a cellulase enzyme and a pectinase enzyme, wherein the cellulase and pectinase enzymes degrade the cellulosic and pectin constituents, respectively, contained in the ingested botanical, to obtain an enhanced quantity of extractable substance from the botanical. In another method of use embodiment, this invention comprises the step of ingesting the above-mentioned botanical food composition further comprising a hemicellulase enzyme which degrades the hemicellulosic constituents contained in the ingested botanical, to obtain an enhanced quantity of extractable substance from the botanical. In yet another method of use embodiment, this invention comprises the step of ingesting the above-mentioned botanical food composition further comprising a xylanase enzyme which degrades the xylan constituents contained in the ingested botanical, to obtain an enhanced quantity of extractable substance from the botanical.

This invention also relates to the above-mentioned enzyme composition for human consumption comprising a cellulase enzyme and a pectinase enzyme, and the corresponding botanical food composition of this invention which further comprises a botanical. In another embodiment, the enzyme composition comprises a cellulase enzyme, a pectinase enzyme and a hemicellulase enzyme, and the corresponding botanical food composition further comprises a botanical. More particularly, the precursor enzyme composition of this invention comprises a cellulase enzyme, a pectinase enzyme, a hemicellulase enzyme and a xylanase enzyme, with the corresponding botanical food composition further comprising a botanical.

BACKGROUND OF THE INVENTION

The subject enzyme compositions and botanical food compositions were invented to meet the needs of the numerous people who rely on botanicals such as herbs and roots to supplement their diet. The full potential of these botanicals has not been previously recognized. One reason for this is that the active constituents in such botanicals are held within each plant cell by the cellulosic, pectic, hemicellulosic and/or xylanic cell walls, which must be either broken or made permeable in order to release extractable substances. Ingestion of crude dried botanicals in capsule or tablet form allows for only minimal extraction of such substances in the gastrointestinal tract of a human being, as the powders used in such preparations are comprised mainly of masses of whole, undisturbed cells, which are resistant to degradation by the digestive enzymes endogenous to the gastrointestinal system of human beings.

The enzymes contained in the enzyme compositions and botanical food compositions of the present invention are able to degrade the cellulosic, pectin, hemicellulosic and xylan constituents of the cell walls of the ingested botanical in the gastrointestinal system of a human being, to obtain the release of an enhanced quantity of extractable substance. For example, the cellulase, pectinase, hemicellulase and xylanase enzymes of the enzyme and botanical food compositions of this invention degrade, respectively, the cellulosic, pectin, hemicellulosic and xylan constituents contained in the plant cell walls of the ingested botanical. This degradation leads to the release of extractable substance from the ingested botanical, thereby making an enhanced quantity available in the gastrointestinal system of a human being. Without the presence of the cellulase and pectinase enzymes of the present invention, the plant cell walls of the ingested botanical would not be degraded by the digestive enzymes endogenous to the gastrointestinal tract of a human being. The cellulase enzyme is important because it degrades the primary plant cell wall, which consists of cellulose. The pectinase enzyme is important because it degrades pectin, which is an essential structural constituent in various botanicals. The hemicellulase enzyme breaks the structure of xylans and related compounds, which are usually associated with cellulose and lignin in botanicals. The xylanase enzyme also degrades xylan, which is a structural constituent of many botanicals.

To the best of applicant's knowledge, the enzyme compositions and botanical food compositions of the present invention are the first such compositions that seek to enhance the quantity of extractable substance in the gastrointestinal system of a human being.

These advantages of the present invention are demonstrated further by the description below.

SUMMARY OF THE INVENTION

This invention relates to a method of increasing the yield of extractable substance from a botanical in the gastrointestinal system of a human being. In one method of use embodiment of this invention, the method comprises the step of ingesting an enzyme composition comprising a cellulase enzyme and a pectinase enzyme, wherein the enzyme composition is ingested at approximately the same time as a botanical is ingested so that the cellulase and pectinase enzymes degrade the cellulosic and pectin constituents, respectively, contained in the ingested botanical, to obtain an enhanced quantity of extractable substance from the botanical.

In another method of use embodiment of this invention, the method comprises the step of ingesting the above-mentioned enzyme composition further comprising a hemicellulase enzyme, which degrades the hemicellulosic constituents contained in the ingested botanical, to obtain an enhanced quantity of extractable substance from the botanical.

In still another method of use embodiment, the method comprises the step of ingesting an enzyme composition comprising a cellulase enzyme, a pectinase enzyme, a hemicellulase enzyme and a xylanase enzyme, wherein the enzyme composition is ingested at approximately the same time as a botanical is ingested so that the cellulase, pectinase, hemicellulase and xylanase enzymes degrade the cellulosic, pectin, hemicellulosic and xylan constituents, respectively, contained in the ingested botanical, to obtain an enhanced quantity of extractable substance from the botanical.

In an enzyme composition embodiment of this invention, the enzyme composition for human consumption comprises a cellulase enzyme and a pectinase enzyme. This invention further relates to an enzyme composition for human consumption comprising a cellulase enzyme, a pectinase enzyme and a hemicellulase enzyme. This invention still further relates to an enzyme composition for human consumption comprising a cellulase enzyme, a pectinase enzyme, a hemicellulase enzyme and a xylanase enzyme.

In another method of use embodiment, the present invention relates to a method of increasing the yield of extractable substance from a botanical in the gastrointestinal system of a human being, the method comprising the step of ingesting a botanical food composition comprising a botanical, a cellulase enzyme and a pectinase enzyme, wherein the cellulase and pectinase enzymes degrade the cellulosic and pectin constituents, respectively, contained in the ingested botanical, to obtain an enhanced quantity of extractable substance from the botanical.

In another method of use embodiment, the method comprises the step of ingesting the above-mentioned botanical food composition further comprising a hemicellulase enzyme, which degrades the hemicellulosic constituents contained in the ingested botanical, to obtain an enhanced quantity of extractable substance from the botanical.

In still another method of use embodiment, the invention relates to a method of increasing the yield of an extractable substance from a botanical in the gastrointestinal system of a human being, the method comprising the step of ingesting a botanical food composition comprising a botanical, a cellulase enzyme, a pectinase enzyme, a hemicellulase enzyme and a xylanase enzyme, wherein the cellulase, pectinase, hemicellulase and xylanase enzymes degrade the cellulosic, pectin, hemicellulosic and xylan constituents contained in the ingested botanical, to obtain an enhanced quantity of extractable substance from the botanical.

This invention further relates to a botanical food composition for human consumption comprising a botanical, a cellulase enzyme and a pectinase enzyme.

This invention further relates to a botanical food composition for human consumption comprising a botanical, a cellulase enzyme, a pectinase enzyme and a hemicellulase enzyme. This invention still further relates to a botanical food composition for human consumption comprising a botanical, a cellulase enzyme, a pectinase enzyme, a hemicellulase enzyme and a xylanase enzyme.

This invention still further relates to the above-mentioned botanical food compositions wherein the botanical is selected from the group consisting of astragalus root, echinacea root, feverfew herb, fo-ti root, ginger root, ginkgo biloba leaf, ginseng, gotu kola herb, horsetail herb, milk thistle seed, saw palmetto berry, uva ursi leaf, valerian root, grape seed, garcinia cambosia fruit, garlic bulb, broccoli, cabbage, brussels sprouts, tomato fruit, red clover flower, licorice root, guarana seed, pfaffia paniculata root, green tea leaf, blueberry berry, buchu leaf, chamomile leaf, hops, yerba mate and ephedra. More particularly, the ginseng root botanical is selected from the group consisting of Panax ginseng root and Siberian ginseng root.

This invention also further relates to the above-mentioned botanical food compositions wherein the extractable substance released from the botanical consists of echinacosides from echinacea root, parthenolides from feverfew herb, gingerol from ginger root, ginkgo flavone glycosides from ginkgo biloba leaf, ginsenosides and eleutherosides from ginseng, silica from horsetail herb, silymarin from milk thistle seed, fatty acids from saw palmetto berry, arbutin from uva ursi leaf, isovaleric and isovalerianic acids from valerian root, leucocyanidins from grape seed, hydroxy citric acid from garcinia cambosia fruit, allicin from garlic bulb, lycopene from tomato fruit, genesteine from red clover flower, glycyrrhizin from licorice root, caffeine from guarana seed, pfaffosides from pfaffia paniculata root, catechins from green tea leaf, anthocyanidins from blueberry berry and umulone from hops.

DETAILED DESCRIPTION OF THE INVENTION

The botanical food compositions in accordance with this invention include a botanical, which is defined as a material derived from plant origin. Examples of botanicals that may be used in accordance with the teachings of this invention are astragalus root, echinacea root, feverfew herb, fo-ti root, ginger root, ginkgo biloba leaf, ginseng, gotu kola herb, horsetail herb, milk thistle seed, saw palmetto berry, uva ursi leaf, valerian root, grape seed, garcinia cambosia fruit, garlic bulb, broccoli, cabbage, brussels sprouts, tomato fruit, red clover flower, licorice root, guarana seed, pfaffia paniculata root, green tea leaf, blueberry berry, buchu leaf, chamomile leaf, hops, yerba mate and ephedra.

The extractable substances from the botanicals described in the present invention include ginsenosides, eleutherosides, parthenolides, ginkgo flavone glycosides, silymarin, isovaleric acids, isovalerianic acids, echinacosides, fatty acids, leucocyanidins, hydroxy acids (e.g., hydroxy citric acid), sulfur-containing compounds (e.g., allicin), lycopene, genesteine, arbutin, glycyrrhizin, caffeine, silica, gingerol, pfaffosides, polyphenols (e.g., catechins), anthocyanidins, alpha-acids (e.g., umulone) and combinations thereof.

For instance, echinacosides may be extracted from echinacea root; parthenolides may be extracted from feverfew herb; gingerol may be extracted from ginger root; ginkgo flavone glycosides may be extracted from ginkgo biloba leaf; ginsenosides and eleutherosides may be extracted from ginseng root—i.e., Panax and Siberian ginseng root, respectively; leucocyanidins may be extracted from grape seed; silica may be extracted from horsetail herb; silymarin may be extracted from milk thistle; fatty acids (e.g., caproic, caprylic, capric, lauric, palmitic, and oleic acids and their ethyl esters) may be extracted from saw palmetto berry; arbutin may be extracted from uva ursi leaf, hydroxy citric acid may be extracted from garcinia cambosia fruit; allicin may be extracted from garlic bulb; lycopene may be extracted from tomato fruit; genesteine may be extracted from red clover flower; glycyrrhizin may be extracted from licorice root; caffeine may be extracted from guarana seed; pfaffosides may be extracted from pfaffia paniculata root; catechins may be extracted from green tea leaf; anthocyanidins may be extracted from blueberry berry; umulone may be extracted from hops and valeric and valerianic acids (e.g., isovaleric and isovalerianic acids, respectively) may be extracted from valerian root.

While a further discussion of these and other botanicals is provided in standard references like the *Handbook of Medicinal Herbs*, a brief discussion of some of the listed botanicals is provided herein.

Feverfew herb, also known as *Chrysanthemum parthenium* Pers. (family Asteraceae), is a herb reported to have a variety of effects, including laxative and carminative.

Considered to be one of China's great herbal tonics, Fo-ti root, also known as *Polygonum multiflorum* Thunb. (family Polygonaceae) or *Centella asiatica* (L.) Urb. (family Apiaceae), is described as being useful in a host of restorative treatments. Ginkgo leaf is the leaf obtained from a diaecious gymnosperm belonging to the family Ginkgoaceae, a relative of the Coniferae.

Ginseng root is obtained from the plants Chinese ginseng [*Panax ginseng* C. A. Mey. (family Araliaceae)] and Siberian ginseng [*Eleutherococcus senticosus* (Rupr. & Maxim.) (family Araliaceae)] and is believed to provide benefits because of the extractable substance, saponin glycosides, that it contains.

Horsetail herb, or *Epuisetum arvense* L. (family Equisetaceae), is a plant having a high silica content.

Saw palmetto, also known as *Serenoa repens* (Bartel.) Small (family Arecaceae), produces a berry that contains palmetto oil, which is believed to provide benefits because of the fatty acids and fatty acid esters that it contains.

Valerian root has been used as flavorings and spices, as well as sedatives, such as CNS-depressant and anticonvulsant activities. Valerian root, or *Valeriana officinalis* L. (family Valerianaceae), contains acids (e.g., acetic, formic and valeric), borneol and derivatives (e.g., bornyl formate, bornyl acetate, bornyl butyrate and bornyl isovalerianate), other bicyclic compounds, such as camphene and pinene, and alkaloids, such as chatinine and valerianine.

Buchu leaf, or *Barosma betulina* (Berg.) Bartl. and Wendl. f. (family Rutaceae), contains from about 1 to about 3.5% of buchu oil, which includes among other components pulegone, isopulegone, diosphenol, menthone, isomenthone, limonene, menthanones, diosmin and rutin.

Yerba mate or paraguay tea is obtained from the leaves of *Ilex paraguarienessis* St. Hil. and other species of Ilex (family Aquifoliaceae), and contains caffeine and tannin.

Guarana seed is obtained from *Paullinia cupana* Kunth ex H.B.K. (family Sapindaceae), a vine extensively cultivated in Brazil. It contains guaranine (caffeine), saponin, a volatile oil and paullinitannic acid.

Camomile leaf is obtained from *Matricaria chamomilla* L. (family Asteraceae).

Astragalus root is obtained from a genus of plants (family Leguminoseae), notably *A. mollisimus* (locoweed), grown on the range lands of Western North America.

Echinacea root can be obtained from *Echinacea pallida* (Nutt.) Britt. or *E. angustifolia* DC. (*Brauneria pallida* Nutt.) Britt. It contains inulin, sucrose, betaine, two isomeric 2-methyl tetradecadienes, echinacein, echinacoside (a caffeic acid glycoside), resins and fatty acids.

Ginger root can be obtained from *Zingiber officinate* (family Zingiberaceae), and contains volatile oil, acrid resin and gingerol.

Gotu kola herb can be obtained from *Centella asiatica* (L.). Urb. (family Apiaceae), and contains caffeine, theobromine and a soluble principle, colatin.

Milk thistle seed is obtained from *Silybum marianum* (L.) Gaertner (family Asteraceae), and contains a mixture of constituents called silymarin, which consists of three lignanflavone isomers—silybin, silydianin and silychristin.

Uva ursi leaf is obtained from *Arctostaphylos uva-ursi* (family Ericaceae), and contains antiseptic glycosides, arbutin, methylarbutin and tannins.

Licorice root or glycyrrhia is obtained from *Glycyrrhiza glabra* (family Leguminoseae) and allied species and contains glycyrrhizic acid.

*Pfaffia paniculata* root also known as Brazilian ginseng is obtained from *Pfaffia paniculata*, and contains saponins and pfaffosides.

Green tea leaf is obtained from various genera of the family Theaceae, including Thea (*T. senensis*), Camellia and Gordonia. Green tea, *Thea viridis*, is usually prepared by drying the leaves rapidly immediately after picking, without allowing them to wilt and ferment. Its chief constituent is the alkaloid caffeine.

Ephedra is a genus of shrubs of the family Gnetaceae, including *Epheora equisetina* (*E. sinica*) and *E. vulgaris* var. *Helvetia*. It contains the alkaloid ephedrine, 2-methylamino-1-phenyl-1-propanol.

The botanicals grape seed, red clover flower, garlic bulb, broccoli, cabbage, brussels sprouts, tomato fruit, hops and blueberry berry are well known to those in the art and therefore further descriptions are not provided herein.

An enzyme composition in accordance with this invention comprises a cellulase enzyme and a pectinase enzyme.

The corresponding botanical food composition further comprises a botanical.

A cellulase enzyme is defined as an enzyme which is capable of degrading cellulose. The cellulase enzymes that can be utilized include those obtained from *Aspergillus niger* or *Trichoderma reesei*. *Trichoderma reesei* is also referred to as *Trichoderma viride*. Although the use of a cellulase enzyme from a fungal source is preferred, the invention is not, however, limited by the source of the cellulase enzyme.

A pectinase enzyme is defined as an enzyme which is capable of degrading pectin. Pectinase enzymes are generally obtained from fungal sources such as *Aspergillus niger* or *Rhizopus oryzae*, and a particularly preferred pectinase enzyme is obtained from *Aspergillus niger*. The invention is not, however, limited by the source of the pectinase enzyme.

Although the cellulase and pectinase enzymes may be obtained by culturing the organisms mentioned above, then extracting and purifying the enzyme by known and conventional techniques, it may be more efficient to purchase the enzymes from any one of the following sources: Bio-Cat, Inc., Industrial Drive, Louisa, Va. 23093; Amano International Enzyme Company, Inc., 250 East Zion Crossroads, Troy, Va. 22974.

In a typical botanical food composition containing a botanical, a cellulase enzyme and a pectinase enzyme, the ratio of botanical to enzyme is approximately about 99:1 to 90:10. The same ratio of botanical to enzyme composition should be used when the botanical and enzyme composition are ingested separately. The concentration of enzyme is not critical. However, for reasons of economics, an excessive quantity of enzyme should be avoided, and for reasons of utility, at least the minimum amount to produce satisfactory results should be used. In accordance with the subject invention, the following enzyme concentrations (based on the total botanical food composition) may be used: for the cellulase enzyme, a concentration of at least approximately about 1,560 Filter Paper Unit ("FPU") per gram; and for the pectinase enzyme, a concentration of at least approximately about 525 Apple Juice Depectinase Unit ("AJDU") per gram. FPU and AJDU are standard units of enzyme activity as explained below.

In another embodiment of the invention, the enzyme composition comprises a cellulase enzyme, a pectinase enzyme and a hemicellulase enzyme. The corresponding botanical food composition further comprises a botanical. The botanical, cellulose enzyme and pectinase enzyme of these embodiments are as defined above. The hemicellulase enzyme is defined as an enzyme which is capable of hydrolyzing specific types of hexosans and pentosans, including more or less complex mannans, galactans and xylans. A hemicellulase enzyme that may be utilized includes the hemicellulase enzyme obtained from *Aspergillus niger* or *Trichoderma reesei*, with *Aspergillus niger* being preferred. The invention is not, however, limited by the source of the hemicellulase enzyme. Although the hemicellulase enzyme may be obtained by culturing an organism, then extracting and purifying the enzyme(s) by known and conventional techniques, it may be more efficient to purchase the hemicellulase enzyme from any one of the following sources: Bio-Cat, Inc., Industrial Drive, Louisa, Va. 23093; Amano International Enzyme Company, Inc., 250 East Zion Crossroads, Troy, Va. 22974.

In a typical botanical food composition containing a botanical, a cellulase enzyme, a pectinase enzyme and a hemicellulase enzyme, the ratio of botanical to enzyme is approximately about 99:1 to 90:10. The same ratio of botanical to enzyme composition should be used when the botanical and enzyme composition are ingested separately. The concentration of enzyme is not critical. However, for reasons of economics, an excessive quantity of enzyme should be avoided, and for reasons of utility, at least the minimum amount to produce satisfactory results should be used. In accordance with this embodiment of the subject invention, the following enzyme concentrations (based on the total botanical food composition) may be used: for the cellulase enzyme, a concentration of at least approximately about 1,560 FPU per gram; for the pectinase enzyme, a concentration of at least approximately about 525 AJDU per gram; and for the hemicellulase enzyme, a concentration of at least approximately about 65 Hemicellulase Unit ("HCU") per gram. FPU, AJDU and HCU are standard units of enzyme activity as explained below.

In still another embodiment of the invention, the enzyme composition comprises a cellulase enzyme, a pectinase enzyme, a hemicellulase enzyme and a xylanase enzyme. The corresponding botanical food composition further comprises a botanical. The botanical, cellulase enzyme, pectinase enzyme and hemicellulase enzyme of these embodiments are as defined above. A xylanase enzyme is defined as an enzyme which is capable of degrading xylan. Xylanase enzymes can be obtained from *Trichoderma reesei* or *Aspergillus niger*. The invention is not, however, limited by the source of the xylanase enzyme. Although the xylanase enzyme may be obtained by culturing an organism, then extracting and purifying the enzyme(s) by known and conventional techniques, it may be more efficient to purchase the xylanase enzyme from any one of the following sources: Bio-Cat, Inc., Industrial Drive, Louisa, Va. 23093; Amano International Enzyme Company, Inc., 250 East Zion Crossroads, Troy, Va. 22974.

In a typical botanical food composition containing a botanical, a cellulase enzyme, a pectinase enzyme, a hemicellulase enzyme and a xylanase enzyme, the ratio of botanical to enzyme is approximately about 99:1 to 90:10. The same ratio of botanical to enzyme composition should be used when the botanical and enzyme composition are ingested separately. The concentration of enzyme is not critical. However, for reasons of economics, an excessive quantity of enzyme should be avoided, and for reasons of utility, at least the minimum amount to produce satisfactory results should be used. In accordance with this embodiment of the subject invention, the following enzyme concentrations (based on the total botanical food composition) may be used: for the cellulase enzyme, a concentration of at least approximately about 1,560 FPU per gram; for the pectinase enzyme, a concentration of at least approximately about 525 AJDU per gram; for the hemicellulase enzyme, a concentration of at least approximately about 65 HCU per gram; and for the xylanase enzyme, a concentration of at least approximately about 65 Xylanase Unit ("XU") per gram. FPU, AJDU, HCU and XU are standard units of enzyme activity as explained below.

Another ingredient which can be added, although it is not essential, to the botanical food compositions of the present invention is a carrier material. Suitable carrier materials include potato starch, maltodextrins, modified starches, direct compression tablet excipients such as dicalcium phosphate, calcium sulfate and sucrose. A particularly preferred carrier ingredient is the 10 DE Maltrin M100 maltodextrin from Grain Processing Corporation. Typically, the enzymes are supplied as concentrates containing less than about 10% of maltodextrin as a stabilizing agent.

Various other additives which are conventionally added to the enzyme and botanical food compositions, such as preservatives and the like, may be utilized.

The enzyme compositions and the botanical food compositions of the present invention were designed for use as tablets, capsules or powder food supplements, to be ingested by a human being. The enzyme compositions are intended to be ingested at approximately the same time as a botanical is ingested. This means that the enzyme composition can be ingested either before, during or after ingestion of the botanical, as long as the period of time between the ingestion of the botanical and the enzyme composition is not so great as to prevent the enzymes from degrading the botanical and releasing an enhanced quantity of extractable substance in the gastrointestinal system of a human being.

EXAMPLES

Example 1

In one embodiment, a typical botanical food composition of the present invention comprises the following ingredients: (1) 98% by weight of the botanical ginseng; (2) 1% by weight of cellulase (ex *Aspergillus niger*) containing approximately about 240,000 FPU per gram of cellulase enzyme obtained from Bio-Cat, Inc.; and (3) 1% by weight of pectinase (ex *Aspergillus niger*) containing approximately about 150,000 AJDU per gram of pectinase enzyme, also obtained from Bio-Cat, Inc. The weight percents are weight percentages of the total botanical food composition. FPU and AJDU are standard units of enzyme activity per gram of individual enzyme as explained in more detail below. The enzyme activity per gram of the botanical food composition described in the above example is approximately as follows: cellulase enzyme: about 2,400 FPU/gram; and pectinase enzyme: about 1,500 AJDU/gram.

Example 2

In another embodiment, a typical botanical food composition of the present invention comprises the following ingredients: (1) 97% by weight of the botanical ginseng; (2) 1% by weight of cellulase (ex *Aspergillus niqer*) containing approximately about 240,000 FPU per gram of cellulase enzyme obtained from Bio-Cat, Inc.; (3) 1% by weight of pectinase (ex *Aspergillus niger*) containing approximately about 150,000 ADJU per gram of pectinase enzyme, also obtained from Bio-Cat, Inc.; and (4) 1% by weight of hemicellulase (ex *Aspergillus niger*) containing approximately about 130,000 HCU per gram of hemicellulase enzyme, also obtained from Bio-Cat, Inc. The weight percents are weight percentages of the total composition. FPU, ADJU and HCU are standard units of enzyme activity per gram of individual enzyme as explained below. The enzyme activity per gram of the botanical food composition described in the above example is approximately as follows: cellulase enzyme: about 2,400 FPU/gram; pectinase enzyme: about 1,500 AJDU/gram, and hemicellulase enzyme: about 1,300 HCU/gram.

Example 3

In still another embodiment, a typical botanical food composition of the present invention comprises the following ingredients: (1) 96% by weight of the botanical ginseng; (2) 1% by weight of cellulase (ex *Aspergillus niger*) containing approximately about 240,000 FPU per gram of cellulase enzyme obtained from Bio-Cat, Inc.; (3) 1% by weight of pectinase (ex *Aspergillus niger*) containing approximately about 150,000 AJDU per gram of pectinase enzyme, also obtained from Bio-Cat, Inc.; (4) 1% by weight of hemicellulase (ex *Aspergillus niger*) containing approximately about 130,000 HCU per gram of hemicellulase enzyme, also obtained from Bio-Cat, Inc.; and (5) 1 by weight of xylanase (ex *Trichoderma reesei*) containing approximately about 200,000 XU per gram of xylanase enzyme, also obtained from Bio-Cat, Inc. The weight percents are weight percentages of the total composition. FPU, AJDU, HCU and XU are standard units of enzyme activity per gram of individual enzyme as explained below. The enzyme activity per gram of the botanical food composition described in the above example is approximately as follows: cellulase enzyme: about 2,400 FPU/gram; pectinase enzyme: about 1,500 AJDU/gram; hemicellulase enzyme: about 1,300 HCU/gram; and xylanase enzyme: about 2,000 XU/gram.

Example 4
Panax Ginseng

In this example, the amount of ginsenosides released from Panax ginseng root subjected to an enzyme composition of the present invention was compared to that released from Panax ginseng root without the presence of an enzyme composition, each of which was held under stomach pH and temperature conditions.

Twenty four grams of Panax ginseng root were ground into a powder, from which a twelve gram portion was mixed as a control with 100 mls of distilled water and acidified to a pH of about 4 through the addition of hydrochloric acid. The other ground twelve gram portion of Panax ginseng root was mixed with an enzyme composition of this invention and 100 mls of distilled water. The resulting botanical food composition, excluding the added water, contained 1% by weight of enzyme composition and 99% by weight of the botanical ginseng. This mixture was then acidified to a pH of about 4 through the addition of hydrochloric acid.

Each of these two portions (the control and the botanical food composition) was then incubated for a period of about two hours at a temperature of about 37° C., after which time the mixtures were filtered. The filtrates were then analyzed for total ginsenoside content by the known method described by Lui and Staba in the *Journal of Natural Products* [43(3), 340–46 (May–June 1980)]. The results indicated that about 5.4% (w/v) ginsenosides were present in the mixture that was subjected to an enzyme composition of this invention whereas only 2.56% (w/v) were present in the control mixture. This represents an increase of extractable ginsenosides of about 110%.

The enzyme composition used in this example, which comprised approximately 1 by weight of the botanical food composition, consisted of the following mixture of enzymes: (1) about 65% by weight of cellulase (ex *Aspergillus niger*) containing approximately about 240,000 FPU per gram of cellulase enzyme obtained from Bio-Cat, Inc.; (2) about 35% by weight of pectinase (ex *Aspergillus niger*) containing approximately about 150,000 AJDU per gram of pectinase enzyme, also obtained from Bio-Cat, Inc.; (3) about 5% by weight of hemicellulase (ex *Aspergillus niger*) containing approximately about 130,000 HCU per gram of hemicellulase enzyme, also obtained from Bio-Cat, Inc.; and (4) about 5% by weight of xylanase (ex *Trichoderma reesei*) containing approximately about 200,000 XU per gram of xylanase enzyme, also obtained from Bio-Cat, Inc. These enzyme weight percents are weight percents of the enzyme composition. It is believed that the hemicellulase and xylanase enzymes used contained small side activities of three additional enzymes—pentosanase, mannan depolymerase and beta glucanase, but the quantities of each were not measured. The known enzyme activity per gram of the particular botanical food composition described in the above example is approximately as follows: cellulase enzyme: about 1,560 FPU/gram; pectinase enzyme: about 525 AJDU/gram; hemicellulase enzyme: about 65 HCU/gram; and xylanase enzyme: about 65 XU/gram. FPU, ADJU, HCU and XU are standard units of enzyme activity as explained below.

Example 5
Guarana Seed

In this example, the amount of caffeine released from guarana seeds subjected to an enzyme composition of the present invention was compared to that released from guarana seeds without the presence of an enzyme composition, each of which was held under stomach pH and temperature conditions.

Twenty grams of guarana seeds (*Paullinia cupana* Kunth, family Sapinoaceae) were ground into a powder, from which a ten gram portion was mixed as a control with 100 mls of distilled water and acidified to a pH of about 4 through the addition of hydrochloric acid. The other ten gram portion of ground guarana seeds was mixed with an enzyme composition of this invention and 100 mls of distilled water. The resulting botanical food composition, excluding the added water, contained 1% by weight of enzyme composition and 99% by weight of the botanical guarana seed. This mixture was then acidified to a pH of about 4 through the addition of hydrochloric acid.

Each of these mixtures was then incubated for a period of about two hours at a temperature of about 37° C., after which time the mixtures were filtered. The filtrates were then analyzed for caffeine content by the gravimetric method described in the *National Formulary*. The results indicated that about 2.3% (w/v) caffeine was present in the mixture that was subjected to an enzyme composition of this invention whereas only 1.2% (w/v) was present in the control mixture. This presents an increase of extractable caffeine of over 90%.

The enzyme composition used in this example was the same as that used in Example 4 above. The enzyme activities are therefore the same as mentioned in Example 4 above.

Example 6

Uva Ursi Leaf

In this example, the amount of arbutin released from uva ursi leaf subjected to an enzyme composition of the present invention was compared to that released from uva ursi leaf without the presence of an enzyme composition, each of which was held under stomach pH and temperature conditions.

The uva ursi leaf was ground, from which a portion was mixed as a control with 100 mls of distilled water and acidified to a pH of about 4 through the addition of hydrochloric acid. The other equal portion of ground uva ursi leaf was mixed with an enzyme composition of this invention and 100 mls of distilled water. The resulting botanical food composition, excluding the added water, contained 1% by weight of enzyme composition and 99% by weight of the botanical uva ursi leaf seed. This mixture was then acidified to a pH of about 4 through the addition of hydrochloric acid. Each of these mixtures was then incubated for a period of about two hours at a temperature of about 37° C., after which time the mixtures were filtered. The filtrates were then analyzed for arbutin content. The results indicated that about 8.9% (w/v) arbutin was present in the mixture that was subjected to an enzyme composition of this invention whereas only 6.8% (w/v) was present in the control mixture. This represents an increase of extractable arbutin of about 30%.

The enzyme composition used in this example was the same as that used in Example 4 above. The enzyme activities are therefore the same as described in Example 4 above.

A FPU unit (Filter Paper Unit) is defined as that quantity of enzyme required, under the conditions of the assay stated in Ghose, T. K., Measurement of Cellulase Activity, IUFAC Commission on Biotechnology (1984). The cellulase in the sample hydrolyses the substrate which is filter paper, and the reducing sugars thus released are assayed spectrophotometrically using dintrosalicyclic acid. An AJDU unit (Apple Juice Depectinase Unit) is based on the time required to depectinize an unclarified apple juice substrate at pH 3.5 and 45° C. The end point is determined by isopropyl alcohol precipitation. An AJDU unit is then determined by correlating depectinization time to the unknown sample with that of a pectinase standard of known activity using a defined single strength apple juice substrate according to procedure number 400.16 (dated May 22, 1992) of Solvay Enzymes, Inc., P.O. Box 4226, Elkhart, Ind. 46514-0226. A HCU unit (Hemicellulase Unit) is that activity that will produce a relative fluidity change of 1 over a period of five minutes in a defined locust bean gum substrate under conditions specified in the assay described in *Food Chemicals Codex*, Third Edition, *General Tests and Apparatus, Hemicellulase Activity*, pp. 490–41. This assay is based on the enzymatic hydrolysis of the interior glucosidic bonds of a defined locust bean gum substrate at pH 4.5 and 40° C. The corresponding reduction in substrate viscosity is determined with a calibrated viscometer. A XU unit (Xylanase Unit) is defined as the activity which liberates one micromole of reducing sugar per minute under conditions of the assay described in Solvay Enzymes, Inc. procedure number 400.101. This assay is based on a 15 minute hydrolysis of xylan at 50° C. and pH 6.0. The reducing sugars liberated are determined with Nelson-Somogyi-Reagent.

In order to make an enzyme or botanical food composition in accordance with this invention, the purified enzymes, with or without the botanical, are dry-blended until a uniform mixture is obtained.

The enzyme and botanical food compositions of this invention are ingested in the same manner as any food product.

The enzyme and botanical food compositions of the present invention are illustrated by way of the above examples which are presented for illustration and not for purposes of limiting the scope of the invention. The invention is not to be limited except as set forth in the following claims.

What is claimed is:

1. A method of increasing the yield of an extractable substance from a botanical in the gastrointestinal system of a human being, the extractable substance and the botanical being selected, respectively, from the group consisting of echinacosides from echinacea root, parthenolides from feverfew herb, gingerol from ginger root, ginkgo flavone glycosides from ginkgo biloba leaf, ginsenosides and eleutherosides from ginseng, silica from horsetail herb, silymarin from milk thistle seed, fatty acids from saw palmetto berry, arbutin from uva ursi leaf, isovaleric and isovalerianic acids from valerian root, leucocyanidins from grape seed, hydroxy citric acid from garcinia cambosia fruit, allicin from garlic bulb, lycopene from tomato fruit, genesteine from red clover flower, glycyrrhizin from licorice root, caffeine from guarana seed, pfaffosides from pfaffia paniculata root, catechins from green tea leaf, anthocyanidins from blueberry berry, umulone from hops, buchu oil from buchu leaf, caffeine from yerba mate and ephedrine from ephedra, said method comprising the step of ingesting an enzyme composition comprising a cellulase enzyme, a pectinase enzyme, a hemicellulose enzyme and a xylanase enzyme at approximately the same time as the botanical is ingested to increase the yield of said executable substance from said botanical in the gastrointestinal system.

2. The method of claim 1, wherein the botanical is ginseng and the extractable substance is ginsenosides.

3. The method of claim 1, wherein the botanical is guarana seed and the extractable substance is caffeine.

4. The method of claim 1, wherein the botanical is echinacea root and the extractable substance is echinacosides.

5. The method of claim 1, wherein the botanical is ginger root and the extractable substance is gingerol.

6. The method of claim 1, wherein the botanical is ginkgo biloba leaf and the extractable substance is ginkgo flavone glycosides.

7. The method of claim 1, wherein the botanical is ginseng and the extractable substance is eleutherosides.

8. The method of claim 1, wherein the botanical is milk thistle seed and the extractable substance is silymarin.

9. The method of claim 1, wherein the botanical is garlic bulb and the extractable substance is allicin.

10. The method of claim 1, wherein the botanical is green tea leaf and the extractable substance is catechins.

11. A method of increasing the yield of an extractable substance from a botanical in the gastrointestinal system of a human being, the extractable substance and the botanical being selected, respectively, from the group consisting of echinacosides from echinacea root, parthenolides from feverfew herb, gingerol from ginger root, ginkgo flavone glycosides from ginkgo biloba leaf, ginsenosides and eleutherosides from ginseng, silica from horsetail herb, silymarin from milk thistle seed, fatty acids from saw palmetto berry, arbutin from uva ursi leaf, isovaleric and isovalerianic acids from valerian root, leucocyanidins from grape seed, hydroxy citric acid from garcinia cambosia fruit, allicin from garlic bulb, lycopene from tomato fruit, genesteine from red clover flower, glycyrrhizin from licorice root, caffeine from guarana seed, pfaffosides from pfaffia paniculata root, catechins from green tea leaf, anthocyanidins from blueberry berry, umulone from hops, buchu oil from buchu leaf, caffeine from yerba mate and ephedrine from ephedra, the method comprising the step of ingesting a composition comprising a cellulase enzyme, a pectinase enzyme, a hemicellulose enzyme and a xylanase enzyme and the botanical to increase the yield of said extractable substance from said botanical in the gastrointestinal system.

12. The method of claim 11, wherein the botanical is ginseng and the extractable substance is ginsenosides.

13. The method of claim 11, wherein the botanical is guarana seed and the extractable substance is caffeine.

14. The method of claim 11, wherein the botanical is echinacea root and the extractable substance is echinacosides.

15. The method of claim 11, wherein the botanical is ginger root and the extractable substance is gingerol.

16. The method of claim 11, wherein the botanical is ginkgo biloba leaf and the extractable substance is ginkgo flavone glycosides.

17. The method of claim 11, wherein the botanical is ginseng and the extractable substance is eleutherosides.

18. The method of claim 11, wherein the botanical is milk thistle seed and the extractable substance is silymarin.

19. The method of claim 11, wherein the botanical is garlic bulb and the extractable substance is allicin.

20. The method of claim 11, wherein the botanical is green tea leaf and the extractable substance is catechins.

* * * * *